United States Patent [19]
Michel

[11] 3,978,856
[45] Sept. 7, 1976

[54] HEART BEAT WAVEFORM MONITORING APPARATUS

[76] Inventor: Walter A. Michel, 433 Hillside Drive, Highland Park, Ill. 60035

[22] Filed: Mar. 20, 1975

[21] Appl. No.: 560,351

[52] U.S. Cl. .............................. 128/2.06 A
[51] Int. Cl.² ............................... A61B 5/04
[58] Field of Search ............... 128/2.06 A, 2.06 B, 128/2.06 F, 2.06 R

[56] References Cited
UNITED STATES PATENTS

| 3,463,143 | 8/1969 | Karsh | 128/2.06 A |
| 3,598,110 | 8/1971 | Edmark | 128/2.06 A |
| 3,618,593 | 11/1971 | Nachev et al. | 128/2.06 A |
| 3,654,916 | 4/1972 | Neilson | 128/2.06 A |
| 3,658,055 | 4/1972 | Abe et al. | 128/2.06 A |
| 3,699,946 | 10/1972 | Michel | 128/2.06 A |
| 3,731,672 | 5/1973 | McIntosh | 128/2.06 A |
| 3,824,990 | 7/1974 | Baule | 128/2.06 A |

Primary Examiner—William E. Kamm
Attorney, Agent, or Firm—John E. Peele, Jr.

[57] ABSTRACT

Disclosed is a heart beat waveform monitoring apparatus for electronically analyzing the heart beat of an individual to recognize the unique characteristics of preventricular contractions and other abnormalities of the heart beat rhythm. The device can detect and warn of the presence of tachycardia as well as prevent false indications of a "heart attack" due to noise. Logic circuits are provided to detect the characteristics of the abnormalities and to actuate an indicator.

7 Claims, 12 Drawing Figures

RATE LOGIC SECTION

QRS LOGIC

POLARITY LOGIC

MISSING BEAT LOGIC

TIME RELATION OF
FOUR SIGNALS

TIME COINCIDENCE
FOR "AND" GATE #1

TIME COINCIDENCE "AND" GATE 2

LOSS OF SIGNAL DETECTOR

PULSE RATE FILTER

HEART BEAT WAVEFORM MONITORING APPARATUS

The invention relates to a compact programmable electronic device usable in a hospital in conjunction with other monitoring equipment or as a portable unit away from the hospital for monitoring the heart beat waveform of an individual and recognizing some of the signs of a potential heart attack. Particularly, the invention relates to an electronic device for sensing electrical signals generated by the individual at selected points of the body, which signals are related to the rate and constancy of the heart beat. The signals are processed electronically to detect variations from normal patterns of abnormalities and to isolate "noise" which can provide false indications of the condition of the individual. When a pattern variation or abnormality occurs, the device, by an indicator responsive to a positive signal, functions to alert the individual to take precautions as necessary.

Although the term "heart attack" describes many variations of heart disease which might result in heart failure, particular interest is directed toward the class in which preventricular-contractions or PVC's may lead to catastrophic events, such as ventricular fibrillation, which in turn results in heart failure. With adequate warning to enable obtaining medical treatment, many of the complications due to PVC's can be prevented.

Warning systems for detecting heart beat abnormalities have been proposed primarily for use within hospitals, but even these are inadequate because of their sensitivity to many types of unrelated interference or "noise" generated by normal activites of patients, whether bed-ridden or ambulatory. Hence, in many hospitals equipped with such warning systems, these systems are de-activated by operating personnel due to their extremely high rate of false alarms. The personnel prefer to watch the electro-cardiographic monitors for visual indications of abnormalities. This personal observation results in undesired use of the time of highly trained, relatively high salaried personnel, thereby tending to add to the cost of hospitalization. Hence, an ultimate purpose of this device is to reliably evaluate heart beat signals with minimum chance of false warnings, and to free highly trained personnel for other duties.

For the ambulatory individual, the danger of death due to a "heart attack" can be greatly reduced by a reliable warning system such as the device of this invention. Often, pre-ventricular contractions are present for many hours, without any noticeable physical warning, before a serious situation might develop. Usually, sufficient time is available for the individual to obtain medical attention following the first indications that a heart attack might be imminent.

The cardiac monitor of the present invention is designed to electronically analyze the heart beat of an individual to recognize the unique characteristics of pre-ventricular contractions and other abnormalities of the heart beat rhythm. Such other abnormalities can include the loss of input signals as might occur due to heart failure or loose sensor connections or leads. Further, the device can detect and warn of the presence of tachycardia, which is an extremely rapid palpitation of the heart. These abnormalities are detected by first sensing a constant in the form of a patient's R-wave complex which is generally of normal duration although the frequency thereof may vary due to ordinary causes. Using the QR-rise of an R-wave complex as a starting point, the monitor examines the period between the initiating wave and a next wave for the presence of a pre-ventricular-contraction. By cooperating electronics, such as a "pulse rate filter," other abnormalities such as (tachycardia, are detected. Upon the occurrence of an abnormality, a warning is actuated.

the arrhythmio known as a pre-ventricular-contraction has several unique characteristics which distinguish it from a normal heart beat. A PVC occurs early in the normal rhythm. It is usually larger in terms of its electrical output, and is always wider than the normal heart beat. It has an opposite polarity component significantly greater than the minimum negative showing of a normal heart beat. Further, when a PVC occurs, the next normal heart beat will not be present.

A heart beat monitor according to the present invention is intended to electronically recognize the above mentioned unique characteristics attributable to a PVC. If the actual signal received from a subject were as clean and free of noise as shown in the drawings, any one of the four characteristics could be recognized to know that an irregularity had occured. However, in practice, these signals are often distorted by patient movement or interference of many types. In these cases, it is very undesirable to give a false warning. Therefore, to accurately detect a PVC in an environment of noise and interference, as many as possible of the known unique characteristics should be programmed into this monitor to assure that false warnings will not occur. An innovation of this monitor is that if noise of any source is present, it could conceivably trigger one or more of the first three logic circuits for detecting the PVC characteristics, but the mere fact of its presence would negate the last characteristic which is an absence of signal requirement.

Broadly, the heart beat monitor of the present invention is a computer or logic programmed to receive signals from an individual and to analyze the signals for abnormalities. A rate logic circuit is to recognize a premature beat. A QRS logic circuit is to detect an unusually wide heart beat. A polarity logic circuit is to determine if a negative polarity is present. One or more of these characteristics must occur with respect to one beat. When this requirement is fulfilled, a missing pulse logic must next be actuated to enable an AND gate to indicate that the required criteria have been met and in fact the heart beat being analyzed was a pre-ventricular contraction.

An object of the present invention is to provide a heart beat abnormality monitor having the aforegoing characteristics.

The above and other objects of the invention will be apparent from the following detailed description, considered in connection with the accompanying drawings in which like numerals refer to like parts.

Figure 3:
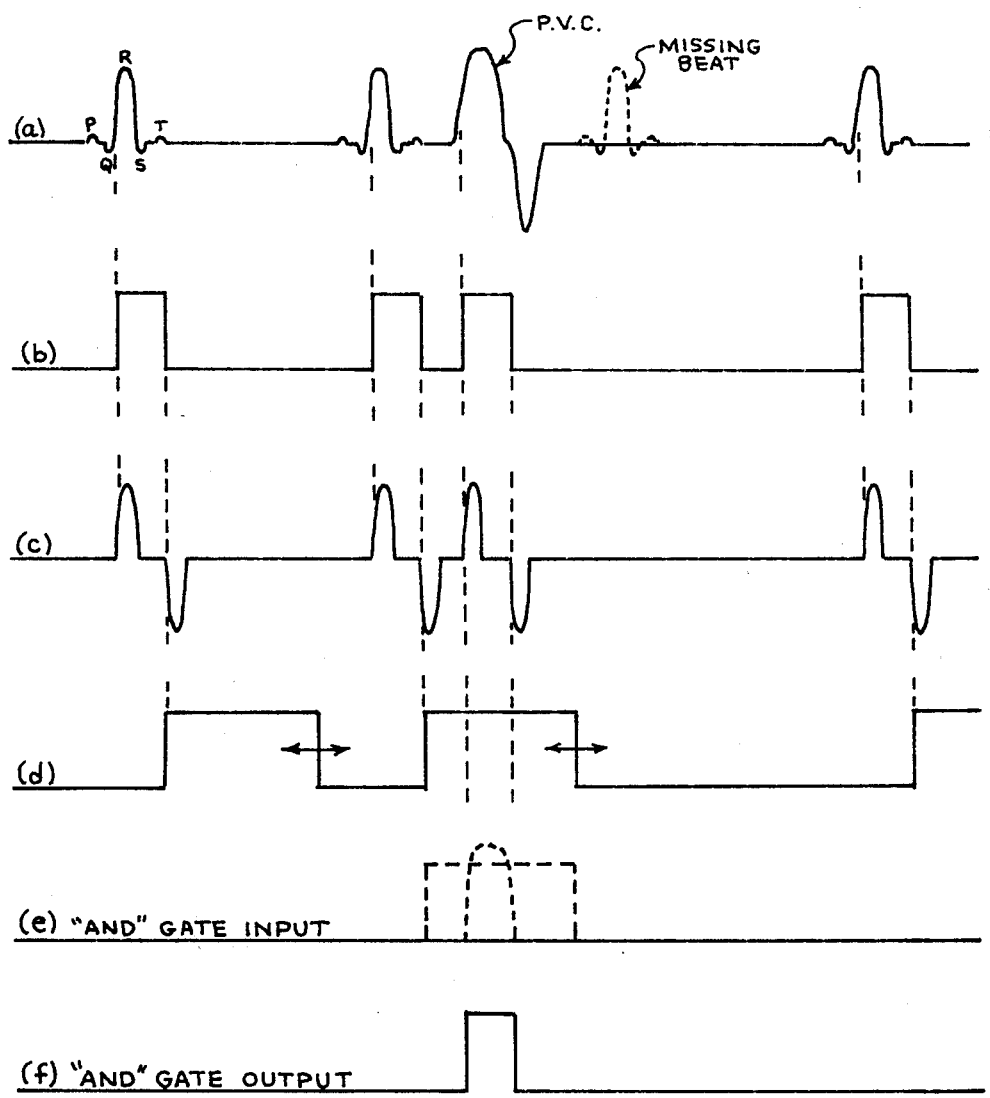
FIG. 3 is a timing diagram of representation of various waveforms useful in explaining the operation of the rate logic section.
Figure 4:
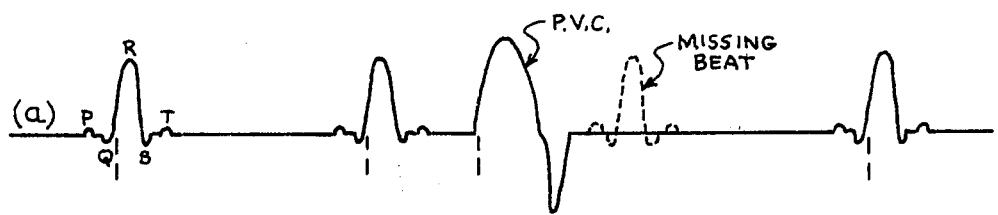
FIG. 4 is a similar representation as that of FIG. 3 with respect to the QRS logic section.
Figure 4:
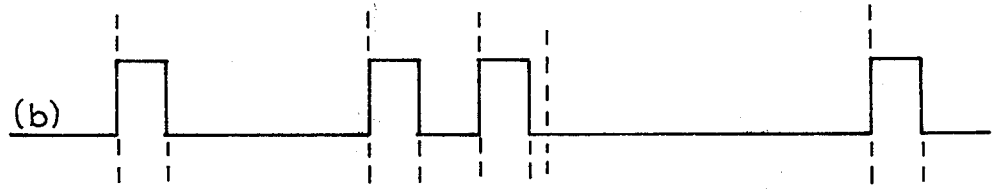
Figure 4:
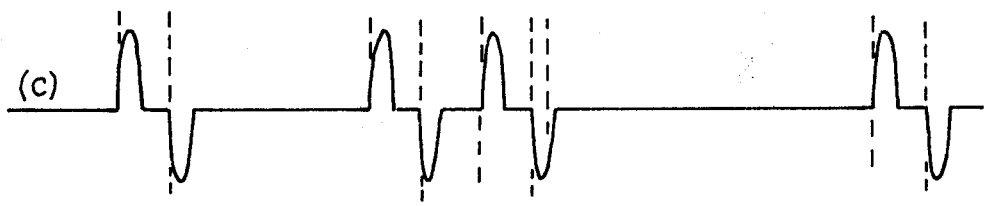
Figure 4:
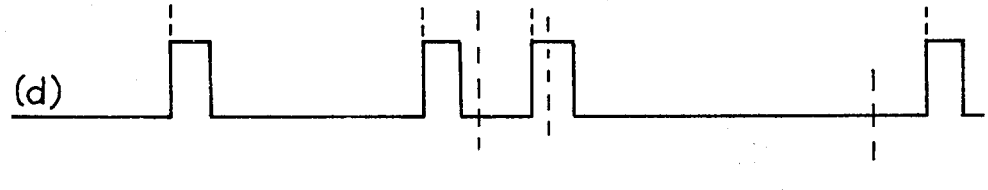
Figure 4:
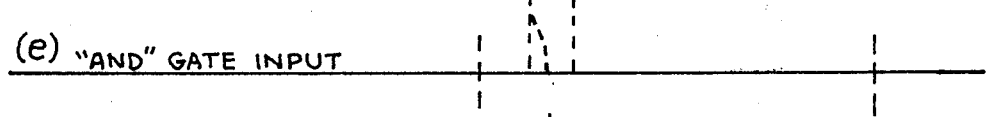
Figure 4:
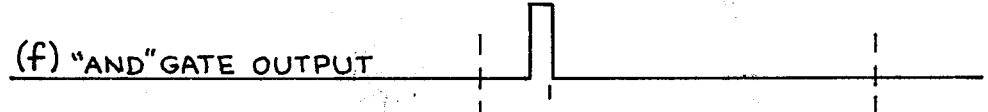

The multi-part figures (FIGS. 3, 4, 7, 8, 9, 10, and 12) are referenced in the specification with the figure number followed by the line identified by an alphabet in parentheses, such as "FIG. 3(a)" which refers to "line a of FIG. 3."

Figure 1:
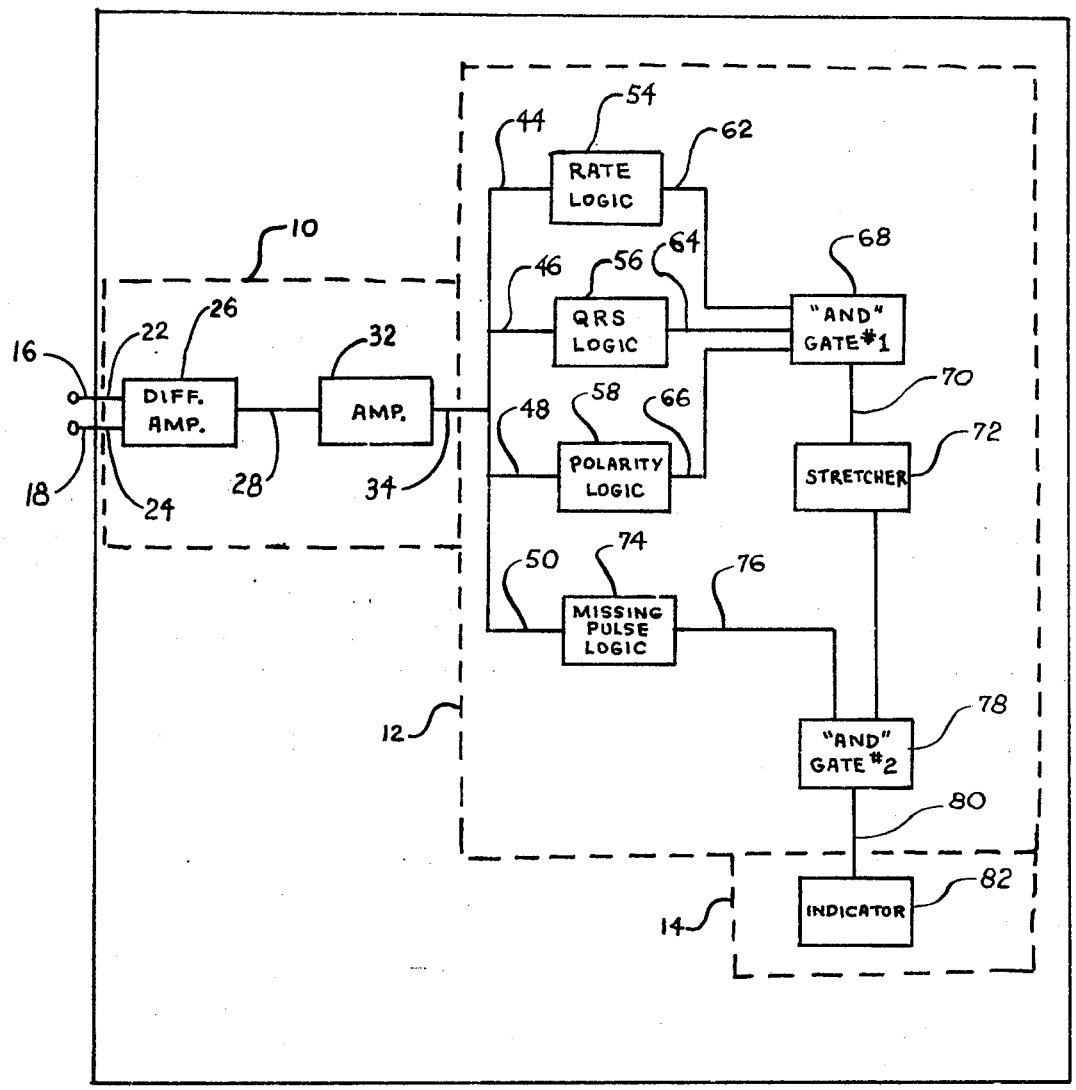
FIG. 1 is a block diagram of the major components of the monitor.

Referring to FIG. 1, a simplified block diagram is shown of the electronic components of the cardiac monitor as attached to an individual or patient (not shown). The monitor includes a pre-amplifier and amplifier section 10, a computer or signal processing section 12 and an output or indicator section 14. Signals are obtained from the patient by a pair of transducing electrodes or sensors 16, 18 of known construction which are placed in contact with the patient at two of the points at which information for electrocardiographic examinations can be taken. These points on the body generate potentials of different parameters, responsive to variations in the heartbeat of the individual. The information can be converted into electrical signals and fed along lines 22, 24 to a differential amplifier 26 which combines the signals to represent a heart beat wave form. The resulting signals of the differential amplifier 26 are fed along line 28 to be amplified by a high gain amplifier 32 which feeds the signals along line 34 to the computer logic or processing circuit section 12. In this section, the waveform is analyzed for the presence of abnormal waveforms or waveform portions and missing waveforms. Upon detection of such abnormal waveform portions, the computer section 12 actuates an indicator or alarm mechanism of the indicator section 14.

Referring now to FIG. 3(a) a typical waveform representative of a series of heart beats is shown. The waveform has been processed through the differential amplifier and enters the computer logic section 12 after being properly amplified in amplifier section 10. The signal passes simultaneously along lines 44, 46, 48, and 50. This computer logic circuit section, as shown in FIG. 1, includes a rate logic circuit 54 which is programmed to recognize the beginning stages of a heart beat whether normal or premature in timing relative to foregoing heart beats. A QRS or width logic circuit 56 analyzes the waveform for the presence of an unusually wide beat such as might be indicative of a PVC. A polarity logic circuit section 58 is programmed to detect a change in polarity of the waveform being analyzed. Upon analyzing of a heart beat, each of the rate logic, the width logic, and the polarity logic circuits generate a pulse when their respective characteristics are detected. The logic circuits are electrically connected respectively by lines 62, 64, and 66 to an AND gate No. 1 at 68 which requires coincidence of each pulse to pass an output pulse or signal. When the requirements are fulfilled, the gate 68 passes the output signal along line 70 to a stretcher circuit 72 so that a pulse is present at the time when the next heart beat would appear.

Another processing portion of the logic section is a missing pulse logic circuit 74 which analyzes the waveform for a missing pulse. This logic circuit is coupled by a lead 76 to the aforegoing circuits through an AND gate No. 2 at 78. Since only a missing pulse will generate an output signal from this logic circuit 74, a pulse is delivered by the second AND gate 78 only when the rate circuit 54, the QRS circuit 56, the polarity circuit 58 and thereafter the missing pulse logic circuit 74 have detected their respective criteria. Hence, the presence of a pulse output from the second AND gate 78 indicates that the required criteria have been met and the heart beat being analyzed was a pre-ventricular contraction or PVC. At this time, a pulse is transmitted along lead line 80 to an indicator 82 in the indicating section 14 of the waveform monitoring and analyzing circuit.

Figure 2:
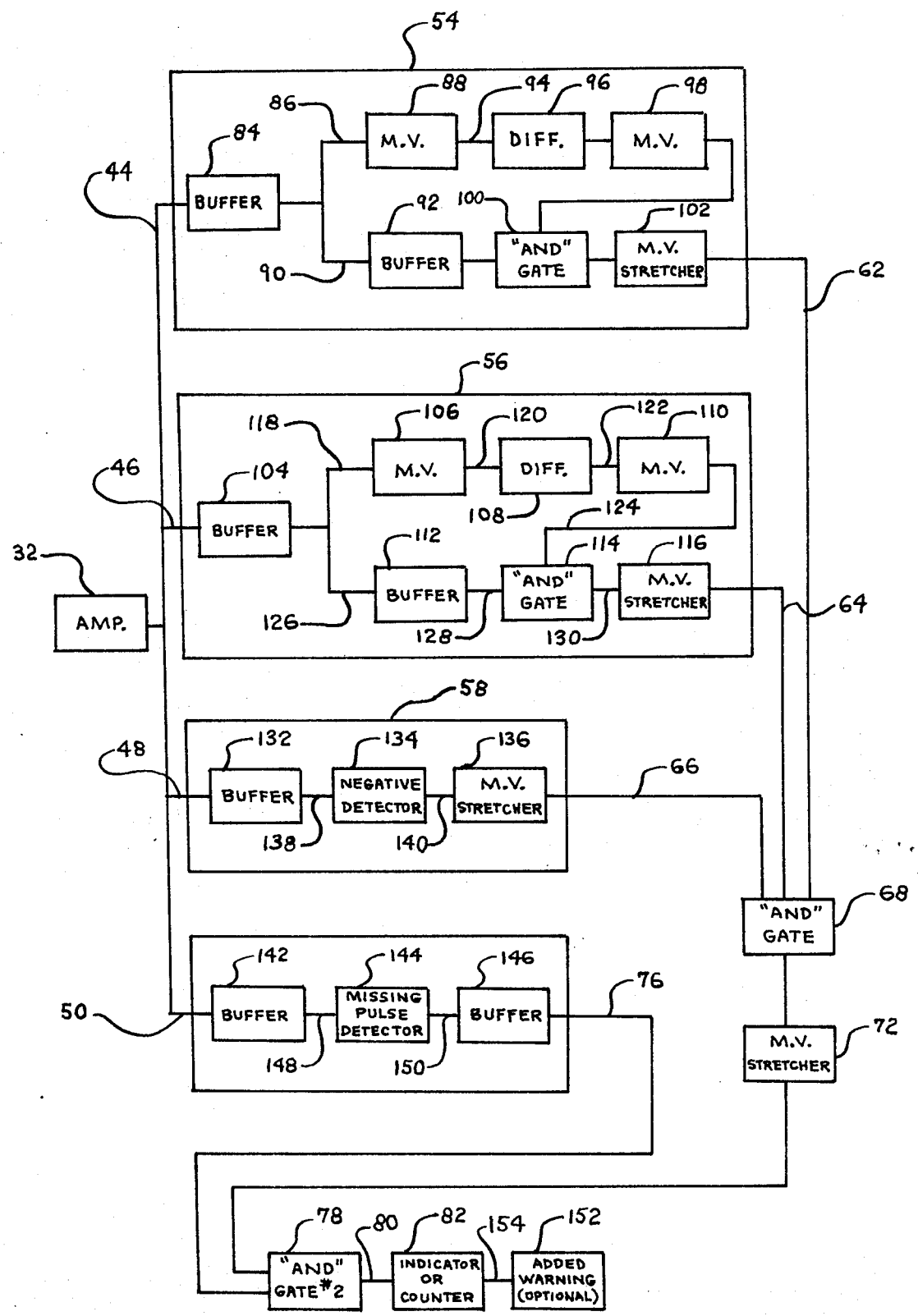
FIG. 2 is a more detailed block diagram of the logic circuits of the monitor of FIG. 1.

Referring to FIG. 2, the rate logic circuit 54 of this heart beat waveform analyzer is described in more detail. This circuit receives a heart beat signal as shown in FIG. 3(a) and transforms the signal as shown in other portions of FIG. 3. As the signal passes simultaneously along lines 44, 46, and 48 from the amplifier section 10, the signal on line 44 is fed to the rate logic circuit 54. Initially, the signal is isolated in a buffer 84 and proceeds simultaneously along line 86 to a multivibrator 88 and along line 90 to a buffer 92. The output signal of the multivibrator 88, as seen in FIG. 3(b), passes along line 94 to a differentiator 96. The output of this differentiator 96, which appears in FIG. 3(c), now continues to another multivibrator 98, the output of which is shown in FIG. 3(d). The output of the latter multivibrator 98 is compared in an AND gate 100 to the output of the buffer 92 which signal is the slightly delayed initial signal of FIG. 3(a). If the two signals are present at the same time, there will be an output from the gate 100 during the time of coincidence as in FIG. 2(f). Thereafter, the output of this gate is processed to a multivibrator stretcher 102. This output signal appears as FIG. 8(a). The output proceeds along line 62 toward AND gate 68 and waits for coincidence with signals from other logic circuits 56 and 58.

A second possible signal for the AND gate 68 proceeded along line 46 to a buffer 104 of the QRS logic circuit 56. From the buffer, the signal goes simultaneously to a multivibrator 106 and to another buffer 112. The output of the multivibrator 106 which passes to differentiator 108 appears in FIG. 4(b). The output of the differentiator 108 appears in FIG. 4(c). This output now continues to a multivibrator 110, the output of which is shown in FIG. 4(d). This output signal of the multivibrator 110 is compared in an AND gate 114 to the output of the buffer 112 which is the signal of FIG. 4(a). If the two signals are present at the same time as shown in FIG. 4(e), there will be an output signal from the AND gate 114 during the time of coincidence as shown in FIG. 4(f). The output of the AND gate 114 is thereafter processed to a multivibrator stretcher 116 as the signal which appears in FIG. 8(b). This output proceeds on line 64 to the AND gate 68 and waits for coincidence with signals on lines 62 and 66.

Figure 5:
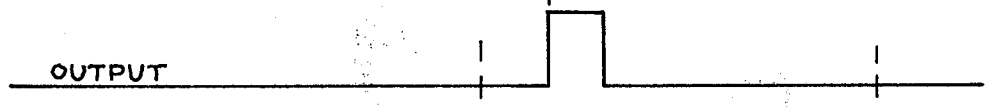
FIG. 5 is a timing diagram of the polarity logic section.

The third possible signal for the AND gate 68 proceeded to the polarity logic circuit 58 from the amplifier section simultaneously with the signals to the rate logic circuit 54 and the QRS logic circuit 56. The signal proceeds along line 48 to a buffer 132. If a negative component of the heartbeat waveform signal is present as in FIG. 4(a), a negative detector circuit 134 will give an output as in FIG. 5. The output of the negative detector circuit is then processed to a multivibrator stretcher 136, which output appears as FIG. 8(c). This output proceeds on line 66 to the AND gate 68, where the signal awaits coincidence with the signals of the other logic circuits.

Should the signals of the rate logic circuit 54, the QRS logic circuit 56, and the polarity logic circuit 58 achieve coincidence at the AND gate 68, this gate produces an output signal as represented in FIG. 8(d). This signal now proceeds to the multivibrator stretcher 72 as the signal shown in FIG. 9(b). This signal now proceeds to the second AND gate 78, where the signal waits for coincidence with the signal from the missing pulse detector logic circuit 74.

Figure 6:
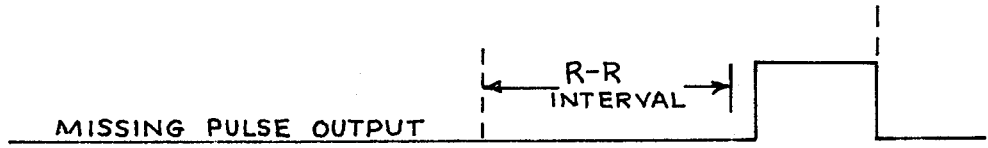
FIG. 6 is a timing diagram of the missing beat logic section.
Figure 7:
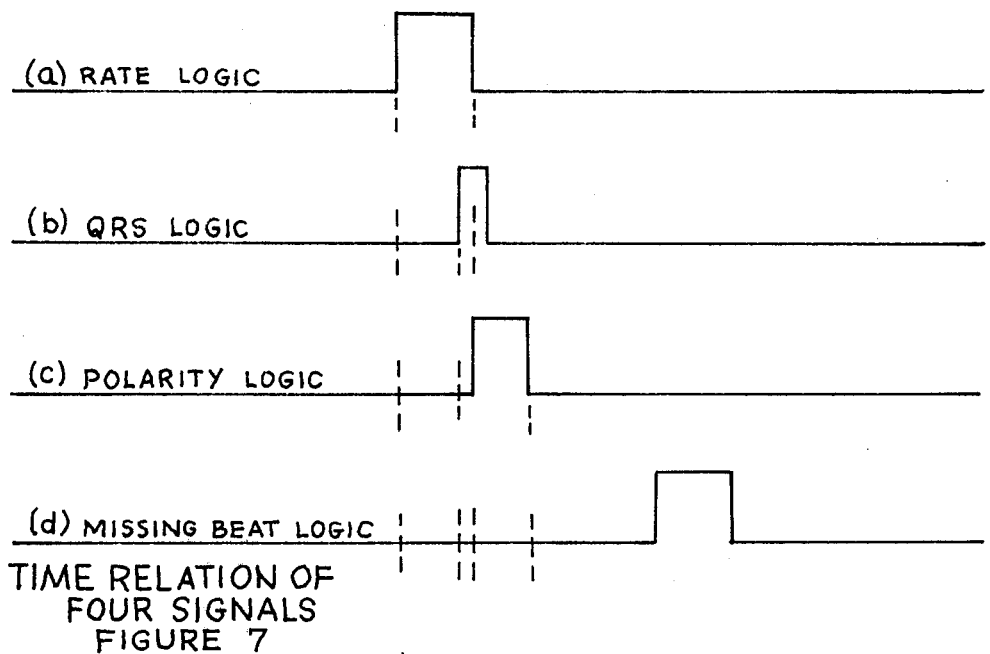
FIG. 7 is a timing diagram of the signals from the logic sections.
Figure 8:
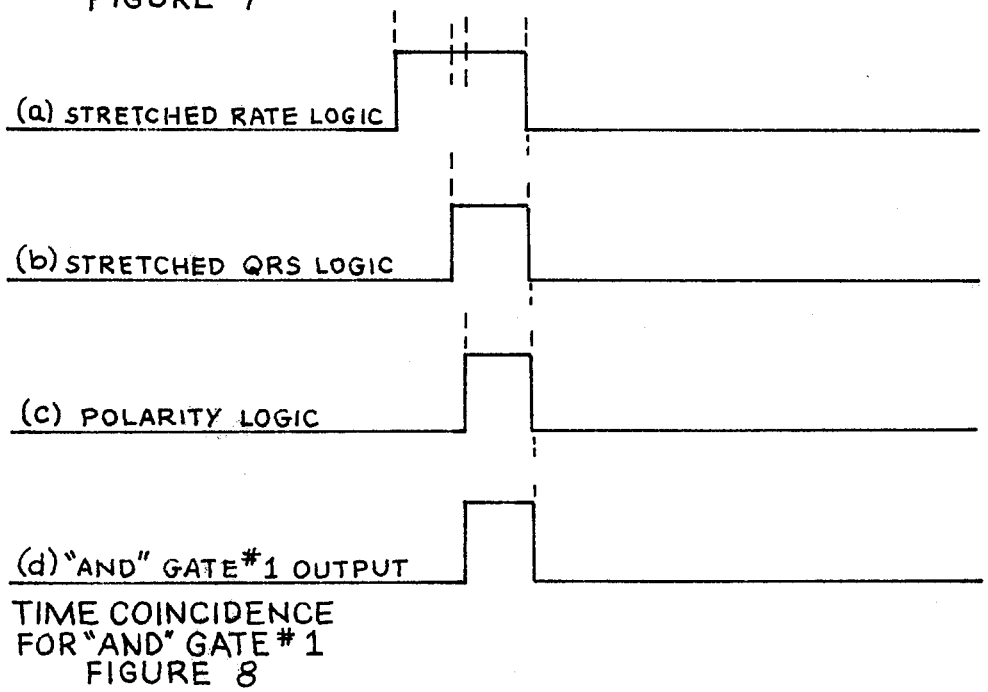
FIG. 8 is a timing diagram for AND gate No. 1.
Figure 9:
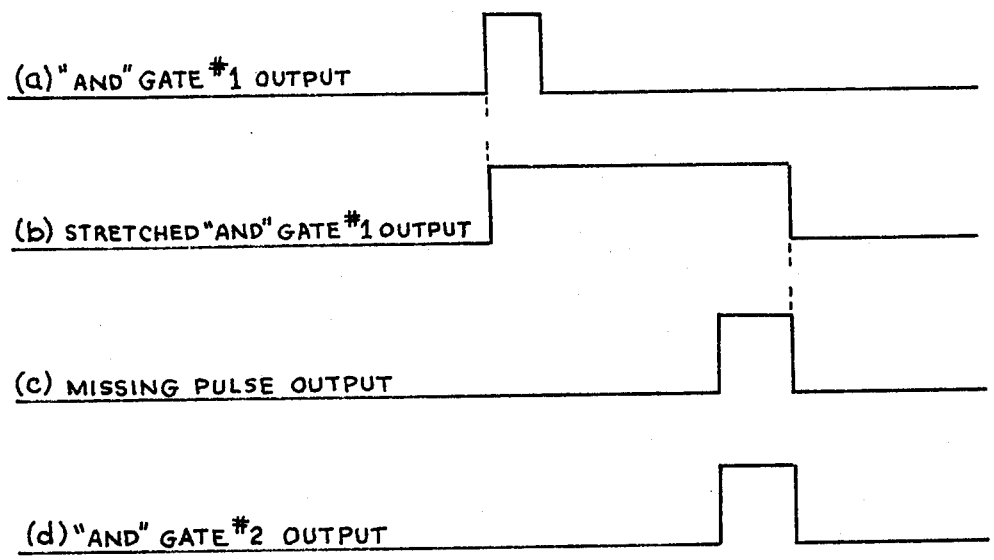
FIG. 9 is a timing diagram for AND gate No. 2.

As the signal from the amplifier section is fed to the aforedescribed logic circuits, a signal portion proceeds along line 50 to the Missing pulse logic circuit 74. The signal into the detector appears as FIG. 4(a). However, there will be no output signal from the circuit unless there is detected the absence of a pulse after a predetermined period of time. Therefore, this circuit gives an output after the PVC plus the normal interval rather than where the missing pulse is noted in FIG. 4(a). This output signal as shown in FIG. 6 proceeds to buffer 146 and along line 76 to the second major AND gate 78.

Since the output signal from the first major AND gate 68 has been stretched as shown in FIG. 9(b), there will be coincidence at the second major AND gate 78 as seen in FIGS. 9(b) and 9(c). When this coincidence occurs, the latter gate 78 will give an output as shown in FIG. 9(d) which proceeds to the indicator section 14 of the monitor. The signal can be used in various ways to indicate the presence of a PVC. Typically, the signal may be used to actuate a counter, an alarm, and/or a piece of equipment such as an EKG recorder.

If noise interference had been present on the signal to the missing pulse logic circuit, there would not have been the absence of a pulse and therefore there would have been no warning. Hence, this circuit makes the system entirely immune to false warnings due to noise and other interference that may have triggered other of the logic circuits.

In order to detect the loss of input signal, the cardiac monitor first senses a constant in the form of the patient's cardiac R-wave complex and its frequency of occurence. The monitor is set at some minimum allowable frequency and if the rate drops below this value, there will be an output from this circuit which will continue until the next heart beat turns it off. Should the interval be longer than the preset minimum, there will be an output between each successive beat.

Figure 10:
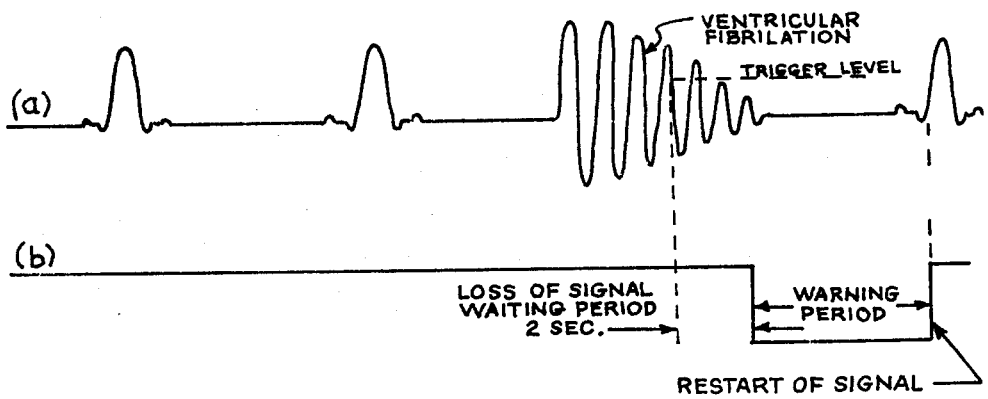
FIG. 10 is a timing diagram and a block diagram of the loss of signal detector.
Figure 10:
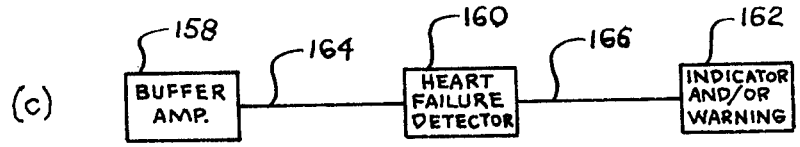

This circuitry will now be described in detail using FIG. 10. The input to the buffer 158 will come from the amplifier 32, and for purposes of this description will appear as FIG. 10(a). The signal will be processed to the "heart failure detector" 160 on line 164, which detector is programmed for a specific rate. So long as this rate is met or exceeded, there will be an output from the detector as shown in FIG. 10(b). However, when there is a loss of signal, the detector output drops to zero which removes a bias from the warning circuit and allows the circuit to activate. When the input signal retruns, the detector output returns and the warning is turned off.

Figure 11:
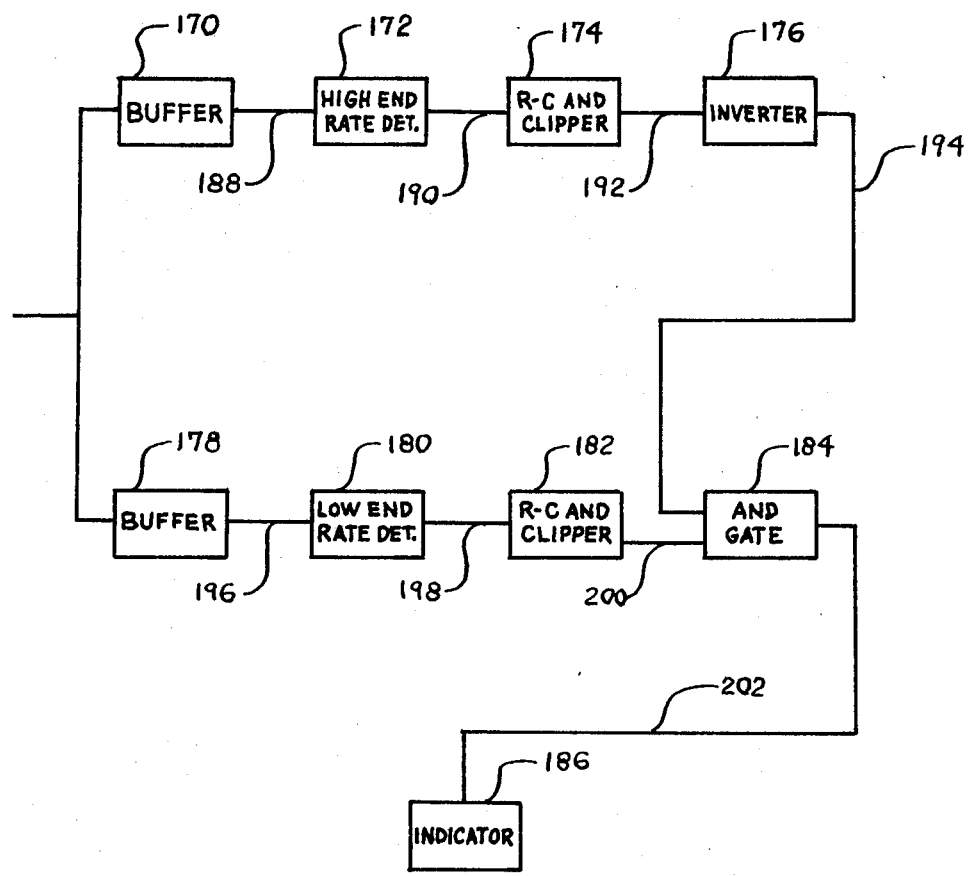
FIG. 11 is a block diagram of a pulse rate filter.
Figure 12:
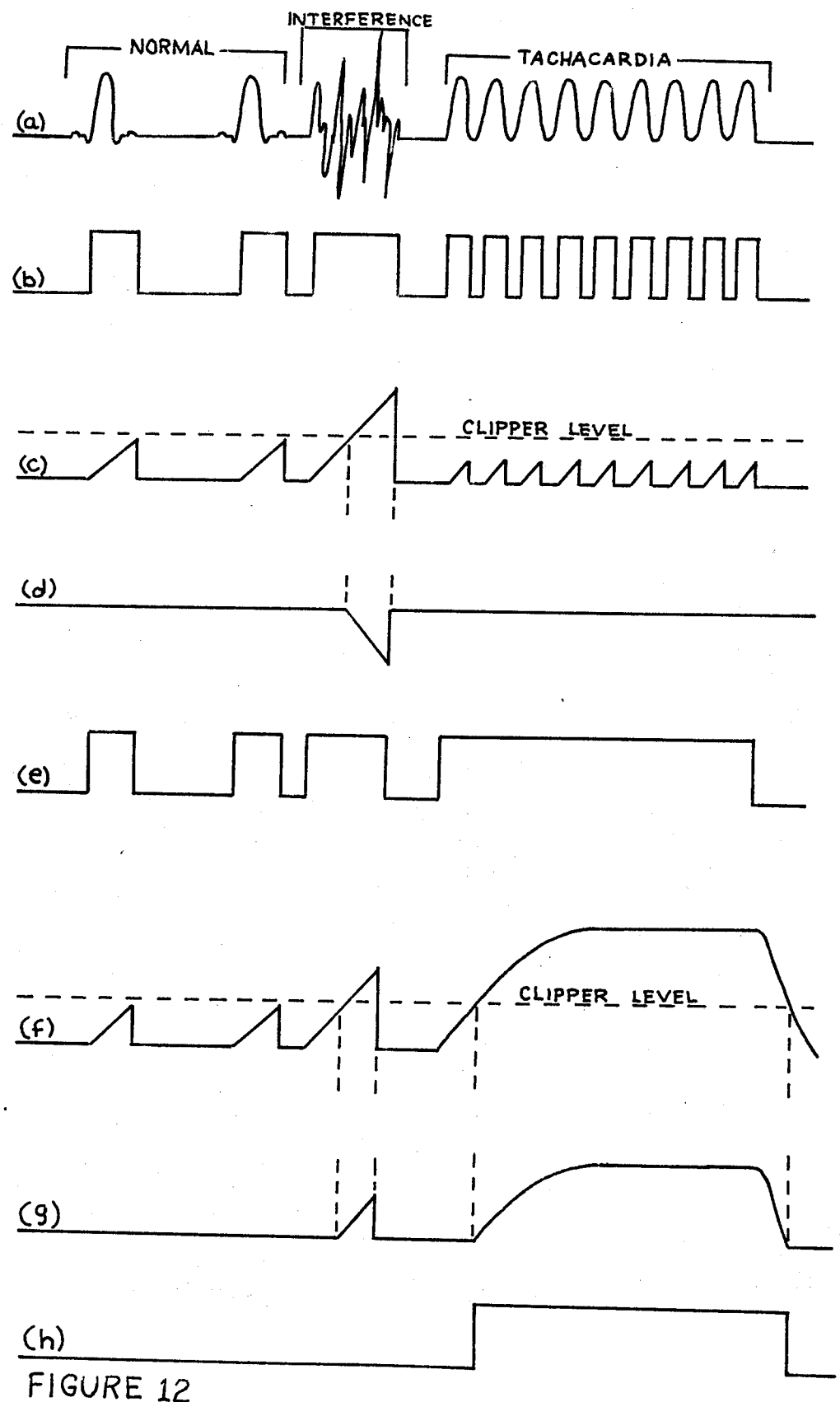
FIG. 12 is a timing diagram relating to a pulse rate filter according to FIG. 11.

Using the timing diagrams of FIG. 12, and the block diagram of FIG. 11, the capability of this monitor to detect ventricular tachycardia is described. The heart beat rate during tachycardia changes suddenly to a rate much higher than the patient's normal heart rate. Ususlly, a rate between 120 and 180 beats per minute would define this phenomena. This circuit brackets the upper and lower limits of the tachycardia rate and only recognizes signals within this range distinguishing this rate from either high rates caused by interference or lower rates in the normal range. Since the normal rate is always lower, it will be ignored. Also, since interference always contains components at a higher rate, this will also be ignored.

The waveform of FIG. 12(a) represents a composite picture of a normal heart beat, interference, and tachycardia. Assume FIG. 12(a) is the input from differential amplifier 26, through amplifier 32 and to the buffers 170 and 178 shown in the circuit of FIG. 11. A "high end rate detector" 172 is programmed to give a negative output each time the rate falls below the upper rate defined as still being tachycardia. Therefore, the output of FIG. 12(b) remains positive only during the presence of interference and falls to a negative or zero level at various points depending on the observed rate. The signal is then processed by the R-C network to integrate the square waves and clip at a proper level as shown in FIG. 12(c). The waveform is then inverted by inverter 176 and processed to an AND gate 184. During this same time interval, buffer 178 passes the input of FIG. 12(a) to the "low end rate detector" 180. This detector is programmed to give a negative output each time the rate goes above the lower rate defined as still being tachycardia. Therefore, the output of FIG. 12(e) remains positive during both the presence of interference and the presence of a tachycardia and falls to a negative or zero level only during the normal rate portion. The signal is then processed by the R-C and clipper network 182 as shown in FIG. 12(f) with a resulting output as shown in FIG. 12(g). The output of FIG. 12(g) is now processed to AND gate 184, where both this signal along line 200 and the earlier described signal on line 194 may arrive in coincidence. Since both signals are positive, the AND gate 184 provides an output to the indicator 186 as shown in FIG. 12(h) as long as the tachycardia lasts. It can now be seen from the waveforms of FIG. 12 that an indication of tachycardia was only given during that actual event and not falsely during the presence of interference or a normal heart beat.

In summary, a portable and programmable electronic heart beat waveform monitor is provided for distinguing from interference and electrical noise the signs of potential heart attack. Hence, a user is adequately warned of heart beat abnormalities with a minimum chance of false warnings. That is, detected abnormalities are isolated from false indicators and analyzed for their respective unique characteristics.

I claim:

1. Heart beat waveform monitoring apparatus for detecting heart beat waveforms by transducers secured to a patient and for analyzing the waveforms for abnormalities, the apparatus comprising:

first logic means for sensing presence of a QR rise in as heart beat waveform and producing a pulse responsive thereto;

second logic means for sensing presnce of an unusually wide QRS heart beat waveform and producing a pulse responsive thereto;

first AND gate means for receiving pulse signals from said first and said second logic means and passing an output pulse upon coincidence of said signals;

other logic means for detecting absence of a heart beat waveform following a first heart beat waveform and producing an output pulse responsive thereto;

second AND gate means for receiving output pulse signals from said first AND gate means and said other logic means; and indicator means connected to said second AND gate means to be activated upon receiving a signal from said second AND gate means.

2. Heart beat waveform monitoring apparatus as in claim 1 wherein said first logic means is a rate logic circuit for receiving and analyzing a heart beat waveform and passing an output signal when a predetermined level of the QR rise is exceeded.

3. Apparatus as in claim 1 wherein output signals of said first logic means and said second logic means are stretched for possible coincidence at said first AND gate with a later output signal from said other logic means for causing passing of an output signal from said AND gate.

4. Heart beat waveform monitoring apparatus for detecting heart beat waveforms by transducers secured to a patient and for analyzing the waveforms for abnormalities, the apparatus comprising:

first logic means for sensing the presence of a QR rise in a heart beat waveform and producing a signal responsive thereto;

second logic means for sensing the presence of an unusually wide QRS heart beat waveform and producing a signal responsive thereto;

third logic means for sensing the absence of a pulse within a predetermined time following said signal generated by said first logic means, and passing a signal; and AND gate means for receiving said signals and passing an output signal when said signals are received in coincidence.

5. Apparatus as in claim 4 wherein said output signal of said first logic means is generated when a predetermined input signal strength is exceeded, and said output signal of said second logic means is generated when a wider than usual signal is received; and including means stretching said output signals for possible coincidence at said AND gate with a later output signal from said third logic means for causing passing of an output signal from said AND gate.

6. Apparatus as in claim 4 including a fourth logic means for sensing a negative component in a heart beat waveform and passing an output signal to said AND gate when such component is detected.

7. Apparatus as in claim 4 including a second AND gate means for receiving said signals from said first logic means and said second logic means and passing an output signal when said signals are received in coincidence.

* * * * *